United States Patent [19]

Kaiser et al.

[11] 4,292,314
[45] Sep. 29, 1981

[54] CARDIOACTIVE 12-DEHYDRODIGOXIN-OXIMES

[75] Inventors: Fritz Kaiser, Lampertheim; Klaus Koch, Mannheim; Wolfgang Schaumann, Heidelberg; Wolfgang Voigtländer, Viernheim, all of Fed. Rep. of Germany

[73] Assignee: Boehringer Mannheim GmbH, Sandhofer, Fed. Rep. of Germany

[21] Appl. No.: 151,481

[22] Filed: May 19, 1980

[30] Foreign Application Priority Data

Jun. 28, 1979 [DE] Fed. Rep. of Germany ....... 2926026

[51] Int. Cl.³ .................. C07J 17/00; A61K 31/58
[52] U.S. Cl. .................................. 424/182; 536/7
[58] Field of Search .................... 536/7; 424/182

[56] References Cited

U.S. PATENT DOCUMENTS

| | | | |
|---|---|---|---|
| 3,937,697 | 2/1976 | Stache et al. | 536/7 |
| 4,021,546 | 5/1977 | Bodor | 536/7 |
| 4,166,849 | 9/1979 | Cohnen | 536/7 |

*Primary Examiner*—Johnnie R. Brown
*Attorney, Agent, or Firm*—Sprung, Felfe, Horn, Lynch & Kramer

[57] ABSTRACT

The present invention provides 12-dehydrodigoxin oximes of the general formula:

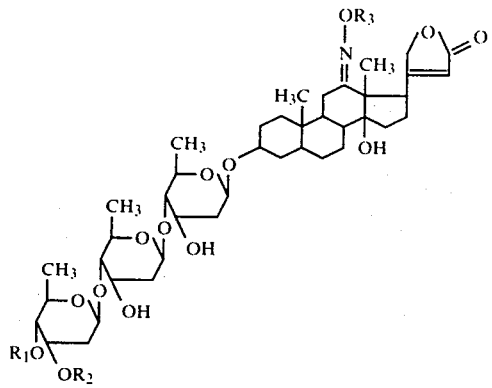

wherein $R_1$ and $R_2$, which can be the same or different, are hydrogen atoms, lower acyl radicals or lower alkyl radicals or $R_1$ and $R_2$ together can represent an alkylidene radical containing 2 to 6 carbon atoms and $R_3$ is a hydrogen atom or a lower alkyl or aralkyl radical. The present invention also provides a process for the preparation of these oximes and pharmaceutical compositions containing them and is also concerned with the use of these oximes for the preparation of pharmaceuticals for the treatment of cardiac insufficiency.

7 Claims, No Drawings

CARDIOACTIVE 12-DEHYDRODIGOXIN-OXIMES

The present invention is concerned with new digoxin derivatives, with the preparation thereof, with pharmaceutical compositions containing them and with the use thereof for the preparation of pharmaceuticals for the treatment of cardiac insufficiency.

The new digoxin derivatives according to the present invention are 12-dehydrodigoxin oximes of the general formula:

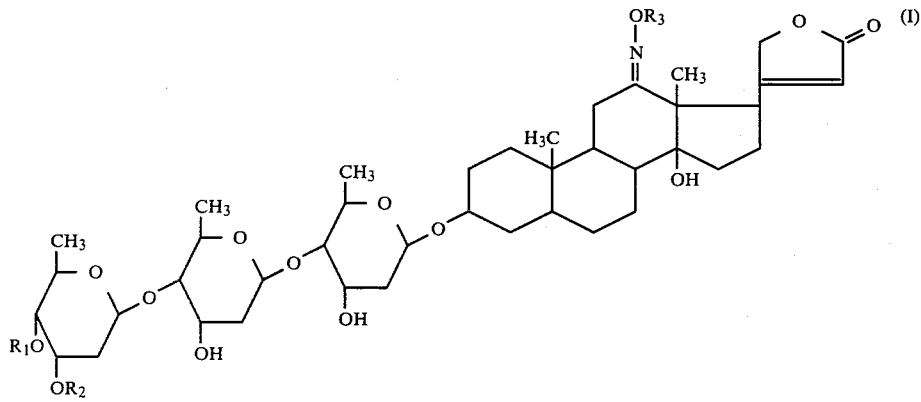

wherein $R_1$ and $R_2$, which can be the same or different, are hydrogen atoms, lower acyl radicals or lower alkyl radicals or $R_1$ and $R_2$ together represent an alkylidene radical containing 2 to 6 carbon atoms and $R_3$ is a hydrogen atom or a lower alkyl or aralkyl radical.

The acyl radicals are to be understood to mean those containing up to 3 carbon atoms, the acetyl radical being preferred, the alkyl radicals are to be understood to mean those containing up to 3 carbon atoms, the methyl radical being preferred, and the aralkyl radicals are to be understood to mean alkyl radicals containing up to 3 carbon atoms which are substituted by a phenyl radical, the benzyl radical being preferred. When $R_1$ and $R_2$ together represent an alkylidene radical, this is preferably an ethylidene, propylidene-1, propylidene-2 or cyclohexylidene radical.

The new compounds (I) according to the present invention can be prepared in known manner, for example, by reacting a compound of the general formula:

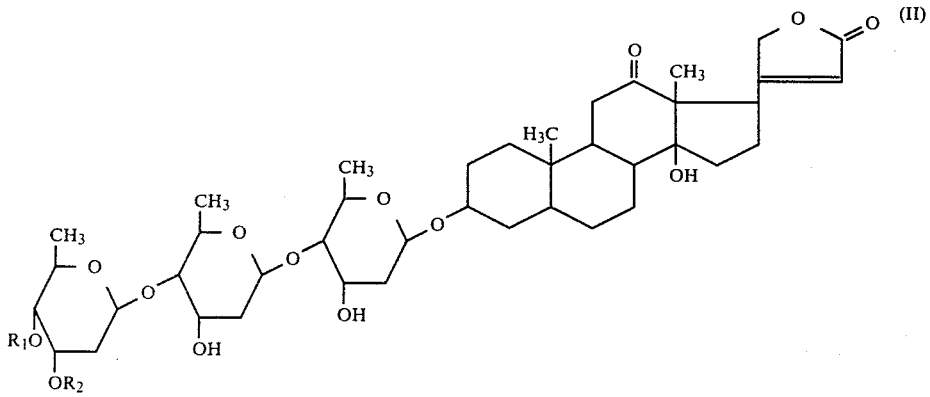

in which $R_1$ and $R_2$ have the same meanings as above, dissolved in an inert solvent, with a hydroxylamine hydrochloride of the general formula:

$$R_3—O—NH_2 \qquad (III)$$

in which $R_3$ has the same meaning as above, in the presence of a weak base.

The compounds of general formula (II) are preferably reacted in a basic solvent, for example, dimethylaniline, triethylamine or pyridine, optionally in admixture with a lower alcohol, preferably ethanol, an additional base thereby being dispensible. The reaction can be carried out at a temperature of from ambient temperature to the boiling temperature of the solvent, the reaction time being from 72 hours to 1 hour.

The end products obtained can be purified by recrystallization or by chromatographic separation or by multiplicative partitioning with subsequent crystallization.

The introduction or conversion of substituents $R_1$ and $R_2$ in the terminal digitoxose can, if desired, also be carried out in known manner after the 12-oximation has taken place.

Thus, for example, an alkyl radical can be introduced by reaction with a diazoalkane, an alkyl halide or a sulphuric or sulphonic acid alkyl ester, an acyl radical can be introduced by reaction with an active acid derivative, for example with an acid chloride or an acid anhydride, and the alkylidene radical can be introduced by reaction with an appropriate aldehyde or ketone, preferably with acidic catalysis.

The following examples are given for the purpose of illustrating the present invention:

Thin layer chromatograms:
TLC-finished plate Merck, silica gel 60/F 254
TLC elution agent I:
  xylene-methyl ethyl ketone 2:3 v/v +5% formamide. Impregnation 20% formamide in acetone
TLC elution agent II: chloroform-methyl ethyl ketone 1:3 v/v
detection: trichloroacetic acid-chloramine reagent.
Fluorescence in long-wave UV ($\lambda = 360$ nm)
$R_D$ means the R value, referred to the running path of digoxin $$\left(\text{Example: } \frac{\text{running path of 12-dehydrodigoxin oxime}}{\text{running path of digoxin}}\right)$$

$R_{DD}$ means the R value referred to the running path of the corresponding digoxin derivative $$\left(\text{Example: } \frac{\text{running path of 12-dehydro-}\beta\text{-methyldigoxin oxime}}{\text{running path of }\beta\text{-methyldigoxin}}\right)$$

EXAMPLE 1

12-Dehydrodigoxin oxime 3 g. 12-Dehydrodigoxin, dissolved in 60 ml. anhydrous pyridine and 60 ml. anhydrous ethanol, are, after the addition of 600 mg. hydroxylamine hydrochloride, heated under reflux for 6 hours. Subsequently, the reaction mixture is diluted with 1.2 liters of water, shaken out six times with one tenth of the volume of chloroform and the combined chloroform phases washed with 2 N sulphuric acid, aqueous sodium carbonate solution and water, dried over anhydrous sodium sulphate and evaporated in a vacuum. The residue is crystallized from chloroform-diethyl ether-petroleum ether to give 2.5 g. 12-dehydrodigoxin oxime; m.p. 172°–176° C.
  TLC elution agent I: $R_D = 2.0$
  TLC elution agent II: $R_D = 1.28$.

EXAMPLE 2

12-Dehydro-$\alpha$-methyldigoxin oxime 1 g. 12-Dehydro-$\alpha$-methyldigoxin, dissolved in 10 ml. anhydrous pyridine and 20 ml. anhydrous ethanol, is, after the addition of 500 mg. hydroxylamine hydrochloride, boiled under reflux for 2 hours, whereafter the reaction mixture is worked up in the manner described in Example 1. The crude product obtained is separated with cyclohexane-ethyl acetate (2:3 v/v) over a column of cellulose impregnated with formamide. The chromatographically uniform fractions give, after crystallization from chloroform-diethyl ether-petroleum ether, 460 mg. 12-dehydro-$\alpha$-methyldigoxin oxime; m.p. 162°–166° C.
  TLC elution agent I: $R_D = 2.79$; $R_{DD} = 1.33$
  TLC elution agent II: $R_D = 1.96$; $R_{DD} = 1.23$

EXAMPLE 3

12-Dehydro-$\beta$-methyldigoxin oxime 3 g. 12-Dehydro-$\beta$-methyldigoxin, dissolved in 60 ml. anhydrous pyridine and 60 ml. anhydrous ethanol, are, after the addition of 600 mg. hydroxylamine hydrochloride, reacted and worked up in the manner described in Example 1. The crude product is separated with cyclohexane-ethyl acetate (1:1 v/v) over a column of cellulose impregnated with formamide. The chromatographically uniform fractions give, after recrystallization from chloroform-diethyl ether-petroleum ether, 2.2 g. 12-dehydro-$\beta$-methyldigoxin oxime; m.p. 151°–154° C.
  TLC elution agent I: $R_D = 2.84$; $R_{DD} = 1.28$
  TLC elution agent II: $R_D = 2.03$; $R_{DD} = 1.22$

EXAMPLE 4

12-Dehydro-3''',4'''-isopropylidenedigoxin oxime 1 g. 12-Dehydro-3''',4'''-isopropylidenedigoxin, dissolved in 10 ml. anhydrous pyridine and 20 ml. anhydrous ethanol, is, after the addition of 500 mg. hydroxylamine hydrochloride, reacted and worked up in the manner described in Example 2. The crude product is separated with cyclohexane-ethyl acetate (3:1 v/v) over a column of cellulose impregnated with formamide. The chromatography uniform fractions give, after crystallization from chloroform-diethyl ether-petroleum ether, 430 mg. 12-dehydro-3''',4'''-isopropylidenedigoxin oxime; m.p. 234°–237° C.
  TLC elution agent I: $R_D = 3.57$; $R_{DD} = 1.06$
  TLC elution agent II: $R_D = 2.89$; $R_{DD} = 1.16$

EXAMPLE 5

12-Dehydro-$\alpha$-acetyldigoxin oxime 1 g. 12-Dehydrodigoxin oxime, dissolved in 20 ml. anhydrous tetrahydrofuran, is, after the addition of 20 ml. triethyl orthoacetate and 2 g. anhydrous zinc chloride, stirred for 6 hours at ambient temperature. Subsequently, the reaction mixture is mixed with 20 ml. water, left to stand for 20 hours at ambient temperature, diluted with 200 ml. water and shaken out six times with one tenth of the volume of chloroform. The combined chloroform phases are washed with water, dried over anhydrous sodium sulphate and evaporated in a vacuum. The residue is separated with cyclohexane-ethyl acetate (2:3 v/v) over a column of cellulose impregnated with formamide. The chromatographically uniform fractions give, after crystallization from chloroform-diethyl ether, 350 mg. 12-dehydro-$\alpha$-acetyldigoxin oxime; m.p. 188°–192° C.
  TLC elution agent I: $R_D = 2.79$; $R_{DD} = 1.38$
  TLC elution agent II: $R_D = 2.0$; $R_{DD} = 1.25$

EXAMPLE 6

12-Dehydro-$\beta$-acetyldigoxin oxime 1 g. 12-Dehydrodigoxin oxime, dissolved in 10 ml. dimethylformamide, is, after the addition of 200 mg. triethylenediamine and 140 g. acetic anhydride, left to stand for 24 hours at ambient temperature. The reaction mixture is subsequently diluted with 100 ml. of water, shaken out with chloroform and the chloroform phases, after washing with 2 N sulphuric acid, aqueous sodium carbonate solution and water, evaporated in a vacuum. The crude product is separated with cyclohexane-ethyl acetate (2:3 v/v) over a column of cellulose impregnated with formamide. The chromatographically uniform fractions give, after crystallization from chloroform-diethyl ether-petroleum ether, 220 mg. 12-dehydro-$\beta$-acetyldigoxin oxime; m.p. 161°–164° C.
  TLC elution agent I: $R_D = 2.84$; $R_{DD} = 1.23$
  TLC elution agent II: $R_D = 2.27$; $R_{DD} = 1.19$

EXAMPLE 7

12-Dehydrodigoxin—O-methyloxime 3 g. 12-Dehydrodigoxin, dissolved in 30 ml. pyridine, are, after the addition of 1.5 g. O-methylhydroxylamine hydrochloride, left to stand for 72 hours at ambient temperature. Subsequently, the reaction mixture is diluted with 1 liter of water, shaken out six times with one tenth volumes of chloroform and the combined chloroform phases are washed with 2 N sulphuric acid, aqueous sodium carbonate solution and water, dried with anhydrous sodium sulphate and evaporated in a vacuum. The residue gives, after crystallization from ethyl acetate-diethyl ether, 2.85 g. 12-dehydrodigoxin-O—methyloxime; m.p. 221°-225° C.

TLC elution agent I: $R_D = 3.84$
TLC elution agent II: $R_D = 1.44$

EXAMPLE 8

12-Dehydrodigoxin-O-ethyloxime 3 g. 12 -Dehydrodigoxin, dissolved in 30 ml. pyridine and 60 ml. anhydrous ethanol, are, after the addition of 1.5 g. O-ethylhydroxylamine hydrochloride, reacted and worked up in the manner described in Example 1. The crude product is separated with cyclohexane-ethyl acetate (2:1 v/v) over a column of cellulose impregnated with formamide. The chromatographically uniform fractions give, after crystallization from acetone-diethyl ether, 720 mg. 12-dehydrodigoxin-O-ethyloxime; m.p. 200°-204° C.

TLC elution agent I: $R_D = 4.08$
TLC elution agent II: $R_D = 1.60$

EXAMPLE 9

12-Dehydrodigoxin-O-benzyloxime 3 g. 12-Dehydrodigoxin, dissolved in 30 ml. pyridine and 60 ml. anhydrous ethanol, are, after the addition of 1.5 g. O-benzylhydroxylamine hydrochloride, reacted and worked up in the manner described in Example 1. The crude product is separated with cyclohexane-ethyl acetate (2:1 v/v) over a column of cellulose impregnated with formamide. The chromatographically uniform fractions give, after crystallization from acetone-diethyl ether, 390 mg. 12-dehydrodigoxin-O-benzyloxime m.p. 222°-225° C.

TLC elution agent I: $R_D = 4.28$
TLC elution agent II: $R_D = 1.57$

EXAMPLE 10

12-dehydro-β-acetyldigoxin-O-methyloxime 3 g. 12-Dehydrodigoxin, dissolved in 30 ml. pyridine, are, after the addition of 1.5 g. O-methylhydroxylamine hydrochloride, reacted and worked up in the manner described in Example 7. The crude product (3.1 g.) is dissolved in 31 ml. dimethylformamide and, after the addition of 630 mg. triethylenediamine and 720 mg. acetic anhydride, reacted and worked up in the manner described in Example 6. The crude product gives, after crystallization from ethyl acetate-diethyl ether, 2.7 g. 12-dehydro-β-acetyldigoxin-O-methyloxime; m.p. 209°-212° C.

TLC elution agent I: $R_D = 4.51$; $R_{DD} = 1.88$
TLC elution agent II: $R_D = 2.24$; $R_{DD} = 1.28$

EXAMPLE 11

12-Dehydro-β-methyldigoxin-O-methyloxime 3 g. 12-Dehydro-β-methyldigoxin, dissolved in 30 ml. pyridine, are, after the addition of 1.5 g. O-methylhydroxylamine hydrochloride, reacted and worked up in the manner described in Example 7. The crude product (3.35 g.) is subjected to multiplicative partitioning with the phase mixture carbon tetrachloride-ethyl acetate-methanol-water (15:1:12:4 v/v/v/v). The aqueous phase gives, after evaporation and crystallization from ethyl acetate-diethyl ether, 2.2 g. 12-dehydro-β-methyldigoxin-O-methyloxime; m.p. 214°-218° C.

TLC elution agent I: $R_D = 3.66$; $R_{DD} = 1.52$
TLC elution agent II: $R_D = 1.45$; $R_{DD} = 0.93$.

The compounds of general formula (I) are new. In contradistinction to digoxin and its corresponding derivatives, they are preponderantly excreted extrarenally and thus offer greater safety when used for cardiac glycoside therapy, especially in the case of patients with reduced kidney function. They are all more lipophilic than digoxin and the corresponding digoxin derivatives, are thus better resorbed and, finally, possess a greater therapeutic spectrum, which follows from the flat dosage/activity curve obtained in the case of injection of increasing dosages of the active materials.

The pharmacological action of the new compounds according to the present invention was determined by the comparison of 12-dehydrodigoxin oxime (Compound 1 from) and 12-dehydrodigoxin-o-methyloxime (Compound 7 from) with digoxin, which is a known pharmaceutical for the treatment of cardiac insufficiency, using the following experimental procedure:

The positive inotropic and cardiotoxic action was tested on cats with pentobarbital-induced heart insufficiency. Increasing dosages were injected at intervals of 10 minutes, so that the total dosage increased in each case by the factor $\sqrt{2}$. The criterion for the therapeutically relevant, positively inotropic action was the increase of the maximum pressure increase rate by 1.5 or 3.0 mm. Hg/sec ($DE_{1.5}$ and $DE_{3.0}$). The quotient from both values is a measure for the steepness of the dosage activity line.

The measure for the cardiotoxicity was the dosage at which the first disturbances of the induction of stimulation took place. The point of time of the commencement of arrhythmias as ascertained from the electrocardiogram and the related dosage calculated by interpolation. The quotient from this cardiotoxic dosage and the $DE_{1.5}$ served as a measure for the therapeutic breadth.

As shown by the results given in the following Table 1, the new compounds according to the present invention had a greater therapeutic spectrum than digoxin. In the case of compound 7, the dosage activity line was also flatter than in the case of digoxin, which can be regarded as being an indication of a better graduation of the activity and thus of a simpler therapeutic use.

Pharmacokinetic investigations were carried out on awake cats, the test compounds being injected intravenously in the $^3$H-marked form. Over the course of 48 hours, blood samples were taken via an implanted catheter for the determination of the radioactivity in the plasma. The urine was collected for 14 days. The elimination constant was calculated from the decrease of the plasma concentration and the amount excreted in the urine. The average values of the therapeutically relevant parameters are summarized in Table 2 hereinbelow.

The lower the total clearance of a compound, the lower is the daily dosage which is needed in order to maintain a definite plasma concentration. The results given in Table 2 hereinbelow show that the products of the present invention had a distinctly lower total clearance. In the case of Compound 1 about 45% and in the case of Compound 7 13% of the dosage of digoxin were needed in order to achieve the same plasma concentration.

The rate of elimination is important for the control of the treatment. In the case of humans, an elimination constant of about 0.015 h$^{-1}$ was found for digoxin, which agrees very well with the results obtained with cats. From the biological point of view, the elimination constant depends upon the total clearance and the distribution volume:

$$\text{elimination constant} = \frac{\text{total clearance}}{\text{distribution volume}}$$

As a result of the lower distribution volume, the elimination constant of Compound 7 was, in spite of the lower total clearance, about equally as great as for digoxin and that of Compound 1 was even greater. This means that the therapeutic activity of the compounds of the present invention can be controlled at least as well as that of digoxin, when disregarding the greater therapeutic spectrum.

A further advantage is the lower excretion quotient in the urine. Toxifications with digoxin occur especially in patients with restricted kidney function. Since the compounds of the present invention are, to a comparatively large extent, eliminated extrarenally, this danger is smaller.

TABLE 1

Positive inotropic and cardiotoxic action of Compounds 1 and 7 in comparison with digoxin in the case of fractionated injection to pentobarbital-insufficient cats A = initial dosage in mg./kg., increasing the total dosage be the factor $\sqrt{2}$ at intervals of 10 minutes.

| test compound | $DE_{1.5}$ mg/kg | $DE_{3.0}$ mg/kg | $\frac{DE_{3.0}}{DE_{1.5}}$ | arrh. mg/kg | $\frac{arrh.}{DE_{1.5}}$ |
|---|---|---|---|---|---|
| digoxin | 0.120 | 0.253 | 2.28 | 0.330 | 2.75 |
| Compound 1 | 0.105 | 0.236 | 1.98 | 0.510 | 4.85 |
| Compound 7 | 0.334 | 0.817 | 3.56 | 1.37 | 4.10 |

TABLE 2

Kinetics of Compounds 1 and 7 in comparison with digoxin in the case of intravenous injection to awake cats

| | digoxin | Cpd. 1 | Cpd. 7 |
|---|---|---|---|
| dosage μg./kg. | 30 | 100 | 100 |
| distribution volume 1/kg. | 13.3 | 2.74 | 1.47 |
| elimination constant h$^{-1}$ | 0.01214 | 0.0258 | 0.0143 |
| renal clearance ml./kg. min. | 1.24 | 0.32 | 0.12 |
| total clearance ml./kg. min. | 2.68 | 1.19 | 0.35 |
| excretion in urine % of dose | 42.8 | 30 | 31 |

The new compounds (I) according to the present invention can be administered enterally or parenterally in liquid or solid form. As injection medium, it is preferred to use water which contains the usual additives for injection solutions, such as stabilizing agents, solubilizing agents and buffers. Additives of this kind include, for example, tartrate and citrate buffers, ethanol, complex formers (such as ethylenediaminetetraacetic acid and its non-toxic salts) and high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavoring and sweetening agents.

The dosage administered can depend upon a variety of factors, such as mode of administration, species, age and/or individual state. In the case of oral administration, the dosage to be administered is from about 0.05 to 1.0 mg. for warm-blooded animals with a body weight of about 70 kg.

It will be appreciated that the instant specification and examples are set forth by way of illustration and not limitation, and that various modifications and changes may be made without departing from the spirit and scope of the present invention.

We claim:

1. A 12-dehydrodigoxin oxime of the formula

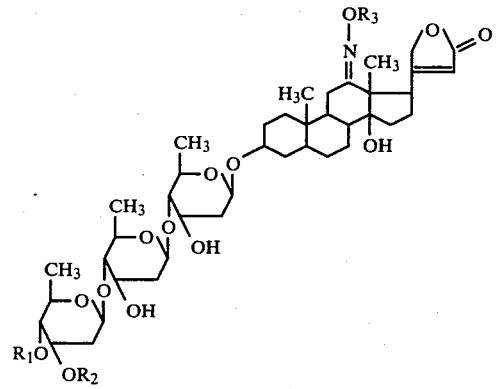

in which
  $R_1$ and $R_2$ each independently is hydrogen, formyl, acetyl, propionyl, methyl, ethyl, n-propyl and isopropyl, or
  $R_1$ and $R_2$ together are ethylidene, propylidene or cyclohexylidene, and
  $R_3$ is hydrogen, methyl, ethyl, n-propyl, isopropyl, benzyl, phenylethyl or phenylpropyl.

2. An oxime according to claim 1, in which
  $R_1$ and $R_2$ each independently is hydrogen or acetyl, or
  $R_1$ and $R_2$ together are ethylidene, propylidene or cyclohexylidene, and
  $R_3$ is hydrogen, methyl or benzyl.

3. An oxime according to claim 1, wherein such compound is 12-dehydrodigoxin oxime.

4. An oxime according to claim 1, wherein such compound is 12-dehydrodigoxin-O-methyloxime.

5. A cardioactive composition comprising a cardioactive effective amount of a compound according to claim 1 in admixture with a pharmacologically acceptable diluent.

6. A method for reducing the cardiac activity of a patient which comprises administering to such a patient enterally or parenterally in liquid or solid form a cardioactive effective amount of a compound according to claim 1.

7. The method according to claim 6, wherein such compound is
  12-dehydrodigoxin oxime or
  12-dehydrodigoxin-O-methyloxime.

* * * * *

UNITED STATES PATENT AND TRADEMARK OFFICE
CERTIFICATE OF CORRECTION

PATENT NO. : 4,292,314
DATED : Sep. 29, 1981
INVENTOR(S) : Fritz Kaiser et al

It is certified that error appears in the above-identified patent and that said Letters Patent are hereby corrected as shown below:

Title Page, [73] Assignee: delete "Sandhofer"

Signed and Sealed this

Twenty-fourth Day of August 1982

[SEAL]

Attest:

GERALD J. MOSSINGHOFF

Attesting Officer    Commissioner of Patents and Trademarks